(12) United States Patent
Prevendar

(10) Patent No.: US 6,652,840 B1
(45) Date of Patent: Nov. 25, 2003

(54) BLEEDING CONTROL AND HEALING AID COMPOSITIONS AND METHODS OF USE

(76) Inventor: Terence Prevendar, 10365 Dearlove Rd., Unit 1D, Glenview, IL (US) 60025-3618

( * ) Notice: Subject to any disclaimer, the term of this patent is extended or adjusted under 35 U.S.C. 154(b) by 85 days.

(21) Appl. No.: 10/072,772

(22) Filed: Feb. 8, 2002

Related U.S. Application Data

(60) Provisional application No. 60/270,379, filed on Feb. 21, 2001.

(51) Int. Cl.$^7$ .............................. A61K 6/00; A61K 9/00; A61K 33/06; A61K 33/26; A61K 3/1717
(52) U.S. Cl. ...................... 424/49; 424/54; 424/400; 424/422; 424/435; 424/484; 424/488; 424/494; 424/520; 424/548; 424/572; 424/647; 424/682; 424/685; 424/698; 514/2; 514/21; 514/57; 514/773; 514/774; 514/777; 514/781; 514/834; 514/801; 514/817; 433/228.1
(58) Field of Search .......................... 424/49, 54, 400, 424/422, 435, 484, 488, 494, 520, 548, 572, 647, 685, 682, 698; 514/2, 21, 57, 773, 774, 777, 781, 834, 801, 817; 433/228.1

(56) References Cited

U.S. PATENT DOCUMENTS

| | | | |
|---|---|---|---|
| 4,395,398 A | | 7/1983 | Yamamoto |
| 4,551,100 A | | 11/1985 | Fischer |
| 4,597,960 A | | 7/1986 | Cohen |
| 4,617,950 A | | 10/1986 | Porteous et al. |
| 4,895,517 A | | 1/1990 | Fischer |
| 5,011,693 A | * | 4/1991 | Whitefield .................. 424/455 |
| 5,447,940 A | | 9/1995 | Harvey et al. |
| 5,635,162 A | * | 6/1997 | Fischer ......................... 424/49 |
| 5,785,955 A | | 7/1998 | Fischer |

OTHER PUBLICATIONS

Chemical Abstracts 126:207324 (1997).*
A Clinical Look at a New Gingival Retraction Material, A Supplement to Compendium of Continuing Education in Dentistry, vol. 23, No. 1 (Suppl), Jan. 2002, Dental Learning Systems, Jamesburg, NJ.

Kerr, We've Sent Cord Packing, downloaded Feb. 18, 2001, www.kerrdental.com/Expa-Syl, p. 1–2.

Kerr, Expa–syl Features & Benefits, downloaded Feb. 18, 2001, www.kerrdental.com/Expa-Syl/Page2.html, pp. 1–2.

Lexi–Comp Inc., Cellulos, Oxidized Regenerated (Dental), downloaded Feb. 18, 2002, www.alternativedr.com/IMCAccess/ProDrugs/CellulosOxidizedRegeneratedDentalpd.., pp. 1–2.

Ethicon, Ethicon Products, downloaded Feb. 18, 2002, www.ethiconinc.com/wound management/wound con.htm, p. 1.

RXMED, Gelfoam Preparations, downloaded Feb. 18, 2001, www.rxmed.com/monographs/gelfoam.html, pp. 1–3.

Medsite, Gelfoam, downloaded Feb. 18, 2000, http://medsite,co.il/drugs/guide/gelfoam.htm, p. 1.

* cited by examiner

*Primary Examiner*—John Pak
(74) *Attorney, Agent, or Firm*—Cook, Alex, McFarron, Manzo, Cummings & Mehler, Ltd.

(57) ABSTRACT

A composition is disclosed which has been shown to stop or control bleeding and seal open small blood vessels while accelerating the healing process of abraded oral "gum" and other "skin" (epithelial) tissues. The composition is preferably in the form of a paste which promotes ease of application and use of the composition. A variety of instruments can be used in application and cleanup of the composition showing versatile unparalleled friendly usage. The composition preferably comprises aluminum chloride, ferric sulfate (subsulfate), regenerated oxidized cellulose, aluminum ammonium sulfate, absorbable gelatin and a solvent. The composition has many dental and medical procedure applications.

8 Claims, No Drawings

BLEEDING CONTROL AND HEALING AID COMPOSITIONS AND METHODS OF USE

This application claims benefit to U.S. Provisional No. 60/270,379 filed on Feb. 21, 2001.

BACKGROUND OF THE INVENTION

The present invention relates to hemostatic compositions and methods for their use, especially in dental procedures. More particularly, the present invention is directed to an improved hemostatic dental composition that can be applied to all dental tissues. In addition, the present invention is directed to hemostatic compositions which are versatile enough to be used to treat most types of soft tissue.

Modern dentistry has become very sophisticated in the use of adhesives. "Bonding" is a word known to most patients. The bonding process is often used to improve the surface of a tooth by applying layers of "synthetic enamel" on the tooth to correct stained or damaged teeth. Blood will ruin the bonding seal to the tooth. Also, blood may be a problem in disease transfer. With bleeding in the dental environment, less is better.

After tissue disruption, such as an extraction, it is important to have the tissues heal and close sooner rather than later. Less patient discomfort allows for further medical and dental procedures to be performed sooner.

Hemostat products have evolved from limited use liquids to more controllable gels, but their applications are limited and may compromise bonding success.

Various hemostats and astringents have been used in dental procedures to control bleeding and aid in retraction of tissue. One of the most common hemostatic and retraction agents used in dentistry is an aqueous solution of aluminum chloride, marketed under a variety of trademarks by several manufacturers. Ferric salts have also been used as astringents, such as ferric subsulfate (Monsel's solution), ferric sulfate, and ferric chloride. A ferric sulfate solution is disclosed in U.S. Pat. No. 4,551,100, for use in the gingival area as a hemostatic agent having both coagulant and astringent properties. The solution was prepared from aqueous ferric sulfate having a concentration of about 6 to 20% in water and glycol. An astringent gel is disclosed in U.S. Pat. No. 4,617,950, which includes an astringent salt and a bodying agent such as carboxypolymethylene.

U.S. Pat. No. 4,395,398 is directed to a liquid dental hemostatic composition which comprises one or more astringents selected from the group consisting of aluminum chloride, tannic acid, ferric chloride, zinc chloride and potassium aluminum sulfate; one or more surfactants selected from the group consisting of cationic surfactants, anionic surfactants and nonionic surfactants; and a carrier or diluent selected from the group consisting of water and a mixture of water and one or more pharmaceutically acceptable water soluble organic solvents.

U.S. Pat. No. 4,597,960 discloses an astringent hemostatic preparation which is provided with a granulated hemostatic (a micron sized inorganic aluminum or ferric salt) encapsulated in a cellulose based, biocompatible polymer which is soluble in body fluids. The composition may be used intra orally or dermatologically. For intra oral purposes, the preferred composition is ferric sulfate microencapsulated in ethyl cellulose material.

U.S. Pat. No. 5,785,955 is directed to hemostatic dental compositions that include an aqueous base, a hemostatic agent that provides astringent action for stopping oral bleeding or providing gingival tissue fluid control, and a chemical binding or coating agent for reducing the acidic activity of the hemostatic agent sufficient to reduce substantial removal of the smear layer plugs in the dentinal tubules of a tooth. A preferred hemostatic agent is a ferric salt compound such as ferric sulphate.

Despite these efforts, there is still a need for an easy to use but versatile, effective, bleeding management solution, especially one that produces fewer side effects, including, but not limited to, avoiding or reducing heart rate stimulation, staining, acid irritations, adhesive interference, and handling difficulties.

Accordingly, it is a general object of the present invention to provide an improved bleeding control composition.

An advantage of the present invention is the provision of a composition which promotes sealing of tissue.

Another advantage of the present invention is the provision of a composition which promotes healing of tissue.

Another advantage of the present invention is the provision of a composition which adheres delicately to most instruments and easily transfers to soft tissue surfaces without remaining on the instrument.

SUMMARY OF THE INVENTION

In accordance with the present invention, a novel composition is provided which acts as a bleeding controller, sealer and healing agent. Compositions of the present invention have been shown to stop bleeding and seal open small blood vessels while accelerating the healing process of abraded oral "gum" and other "skin" (epithelial) tissues. The composition is preferably in the form of a paste which promotes application and use of the composition. The composition preferably comprises aluminum chloride, ferric sulfate (subsulfate), regenerated oxidized cellulose, aluminum ammonium sulfate, absorbable gelatin and a solvent. The composition has many other dental and medical applications. The composition has a pleasant gingerbread appearance and a sour pickle taste.

The present invention address the shortcomings of previous hemostatic alternatives. Compositions of the present invention exhibit versatility. The composition can be formulated as a paste, which applies and rinses away easily.

The composition is preferably a paste and not a liquid or gel, which makes it resistant to spilling or spattering accidents. The paste adheres delicately to most instruments while easily transferring to soft tissue surfaces without remaining on the instrument. To the extent, if any, there is occasional metal reaction on some instruments, the reaction product can be easily buffed away.

When the composition is formulated in the preferred embodiment as a paste it is more user-friendly than liquid or gel type hemostatic products. The product can be applied to cover extraction sites and in addition many other surface and sub-surface tissue applications. The paste can be applied before, during and after dental bonding procedures avoiding the need to redo the procedure.

The composition of the present invention provides other advantages including low tissue irritation, aids in achieving adhesion bonds, and improved healing. The use of the product on gum ulcerations reduces discomfort to the patient. When the need arises because of more difficult bleeding conditions, the paste embodying the present invention can be reapplied as necessary.

Compositions of the present invention stop bleeding problems after scaling or curetage. Patients using coumadin are susceptible to increased bleeding. The product is effective during blood thinner therapy. Moist paste can be readily blotted dry with various products.

Compositions of the present invention have been used in a variety of application procedures and no untoward side effects have been observed. Compositions of the present invention effectively seal bleeding small vessels encountered in all dental procedure situations. Compositions of the present invention can be useful in virtually all dental applications and many medical situations where it is desirable to control bleeding, or to promote tissue sealing or healing.

DETAILED DESCRIPTION OF THE INVENTION

Soft tissues in general are sensitive to caustic agents such as acids. While astringents are useful in checking the bleeding of woods in soft tissues, they can cause inflammation and other patient discomforts or irritation. Hence, the present invention is directed to compositions and methods for providing hemostasis in soft tissues, while being more gentle and less aggressive on the soft tissues than conventional hemostatic compositions.

By using the hemostatic dental composition of the present invention during dental restorative and reconstructive procedures, bleeding can be stopped so that an accurate impression of a tooth can be made. The hemostatic composition of the present invention also has the desirable therapeutic effect of expediting tissue healing.

The present invention provides a hemostatic composition comprising a combination of hemostatic agents selected from a wide variety of hemostatic and astringent compounds. These can include various metal salts such as the salts of aluminum, iron, zinc, manganese, bismuth, etc., as well as other salts containing these metals such as permanganates. Nonlimiting examples of suitable hemostatic agents include ferric sulphate, ferric subsulfate, ferric chloride, zinc chloride, aluminum chloride, aluminum sulfate, aluminum chlorohydrate, and aluminum acetate. Alums such as aluminum potassium sulfate and aluminum ammonium sulfate may also be used. In addition, tannins or other related polyphenolic compounds may be used as the hemostatic agent. The above astringent and hemostatic compounds are acidic in nature and typically have a pH from about 0 to 4.

A preferred hemostatic agent for use in the composition of the invention is a ferric salt compound. Preferred ferric sales include ferric sulphate, which has the formula $Fe_2(SO_4)_3$, and ferric subsulphate, which as the formula $Fe_4(OH)_2(SO_4)_5$. Both ferric and sulfate ions are present within the human body, thus the probability of allergic reactions to ferric sulfate or ferric subsulphate is extremely low. The ferric salts are coagulative hemostats and when contacted with blood, the ferric salts cause instant precipitation of blood proteins, thereby forming a coagulum. Additional preferred hemostatic agents are aluminum chloride and aluminum ammonium sulfate.

Further hemostatic agents, in accordance with the present invention, include oxidized regenerated cellulose such as that commercially available from the Johnson & Johnson Company under the Surgicel® brand name. Oxidized regenerated cellulose is commercially available in the form of a fabric strip. Typically, minimal amounts of the oxidized regenerated cellulose are applied to the bleeding site. There blood saturates the cellulose and the oxidized regenerated cellulose swells into a brownish or black gelatinous mass which aids in the formation of a clot.

Still further hemostatic agents, in accordance with the present invention, include absorbable gelatin such as that commercially available from UpJohn under the GELFOAM brand name. The absorbable gelatin can take the form of a sterile, pliable surgical sponge prepared from specially treated, purified gelatin solution and capable of absorbing and holding within its meshes many times its weight of whole blood.

The hemostatic agents present in the hemostatic compositions are used in an effective amount sufficient enough to provide hemostatic properties to the composition. A preferred composition comprises of aluminum chloride, ferric sulfate (subsulfate), regenerated oxidized cellulose, aluminum ammonium sulfate, and absorbable gelatin. An especially preferred formulation includes the addition of a solvent such as saline solution. The aqueous mixture of these components in the form of a paste is believed to provide molecularly oriented crystals of such components. These crystals produce therapeutic blood clotting, shrinkage of affected tissue swelling, sealing of opened blood vessels, and improved regenerative healing.

While not being limited to any particular theory of the invention, it is believed the components each provide some individual functionality and the components together exhibit a preferred collective functionality. For example, it is believed the aluminum chloride acts as a capillary hemostat; ferric sulfate (subsulfate-option) acts as coagulant; regenerated oxidized cellulose acts as healing hemostat; aluminum ammonium sulfate acts as astringent and filler; absorbable gelatin acts as hydrating hemostat agent; and sterile saline solution acts as astringent solvent.

Preferably the ingredients are combined in the proportions as follows:

Formulation I about 3.6 g (+/−0.3 g) Ammonium aluminum sulfate about 0.1 g (+/−0.03 g) Oxidized regenerated cellulose (e.g., J&J Surgicel)

about 8.0 cc (+/−2.0 cc) 18% (+/−3.5%) ferric sulfate (sub.) solution about 8.0 cc (+/−2.0 cc) 25% (+/−5.0%) aluminum chloride solution More preferably Formulation I also comprises:

about 0.6 g (+/−0.01 g) Absorbable gelatin (e.g., Upjohn Gelfoam) and, optionally, about 2.5 cc (+/−0.5 cc) 0.9% saline solution Preferably the water or solvent content of the composition is adjusted in the manner to provide the composition with a paste like consistency. In that regard, a preferred paste composition can be prepared by combining the components of the composition to form a slurry, dehydrating (or removing the solvent of) the composition by any standard mechanism including but not limited to air drying to form a substantially dry, and most preferably crystalline, composition, and then re-wetting the composition with a sufficient solvent such as, for example saline, for the composition to form the desired paste like consistency. It has been found that a composition prepared according to the preferred Formulation I (containing the absorbable gelatin component) yields about 7.6 g (+/−0.5 g) of a substantially dry composition upon dehydration and that the "dry" formulation can be reconstituted to a paste like consistency by the addition of a solvent, such as saline solution. A preferred paste is made by adding sufficient saline solution to the about 7.6 g (+/−0.5 g) dry crystals to prepare about a 9.5 g (+/<0.5 g) damp, moisturized paste. If the paste becomes too dry for ease of use, it may be re-wet with normal saline, distilled water, or local anesthetic solution, such as, for example, lidocaine, prilocaine, articanine, procaine (novacaine), mepivacaine and bupivacaine local anesthetic solutions. Additionally, the composition may be re-wet by the addition of ferric sulfate (sub) solution and/or aluminum chloride solution. The possibility of an allergic reaction should be considered, of course, if a local anesthetic solution is used as a wetting; or solvent, agent. It will, of course, be appreciated that the amounts of ingredients set forth above are relative amounts and smaller or larger batches can be prepared by appropriate proportioning of the ingredients.

EXAMPLES

Compositions of the preferred Formulation I of the present invention were made in the form of a paste and used in the following applications. In each example a sufficient amount of the paste of the present invention is applied to cover the tissue treated. These examples are intended to be purely exemplary and should not be viewed as limiting the scope of. the invention.

Example 1

Following tooth or root extraction the paste was placed over the optionally packed socket with gauze pressure to form a "bandage" with a suture. Healing time was reduced by four days. Patient experienced little discomfort and insignificant bleeding.

Example 2

Following tooth or root extraction the paste was placed over the optionally packed socket with gauze pressure to form a "bandage" without a suture. Similar results to example 1 were noted.

Example 3

Exposed live tooth "nerve" was "bandaged" with paste to facilitate covering the pulp biocompatibly. The pulp cap nerve showed no "problems" after twelve weeks. Root filling was completed in the initial appointment with uneventful and clinically successful healing.

Example 4

Bleeding root tip apex area was sealed with paste prior to root filling. The root filling hereby was completed in the initial appointment.

Example 5

Between the teeth gum points were sealed with paste after bleeding from cleanings, fillings, or gum disease treatment. The gum tissue healed quickly with little discomfort and no staining of white fillings.

Example 6

Gumline bleeding which occurred during a bonding and luting procedure was arrested by applying paste to allow successful completion. This prevented soft leaky spots between tooth and restorative material caused by blood drop contamination.

Example 7

In impression taking, the present invention my enhance replication of the gum line crevice in addition to controlling bleeding to facilitate impression taking. Prior to taking an impression, paste of the present invention is applied to bleeding along the gum line. An impression is then taken with standard impression material such as, for example but not by way of limitation, hydrocolloid impression material. After the impression material sets, the impression is removed and some of the paste material is incorporated in the impression enhancing the impression.

These are a few of the many already tested applications of the present invention demonstrating the broad versatility of use for the present invention in other dental and medical considerations. Additional features of the present invention include: Compositions of the present invention can be reapplied for deep bleeder applications.

Seals bleeding gums after scaling or curetage.

Following rinsing the present invention will not interfere with dental bonding procedures.

The composition acts as a bandage supplementing and reducing the need for perio dressing.

Compositions of the present invention allow the performance of a variety of gum retraction procedures.

Allows for suture-less minimally invasive closure of dental fistulas.

The paste has been shown to improve healing times in surface tissue application.

Compositions of the present invention exhibit fewer undesirable side effects than alternative agents. These effects include but are not limited to acid irritation, permanent staining and uncontrolled migration.

Depending on the procedure performed, the paste can be cleaned up through the use of water, mild detergent, alcohol, or acetone.

Since this composition can be formulated as a paste and not a gel, it can be precisely placed on the intended areas of treatment without migration.

Helps heal denture sores.

Compositions of the present invention are bacteriostatic, exhibiting a minimum two year shelf life.

The use of compositions of the present invention on gum ulcerations decreases the patient's sensitivity; expedites successful sealing root perforations, exposed pulps and root apex hemorrhage.

The convenience and effectiveness of present invention encourages the use of this product in many different medical and dental applications.

The present invention is not limited to the exemplified embodiments which are considered as illustrative and not restrictive and the present invention may be embodied in other forms, apparent to those of ordinary skill in the art, without departing from the spirit or essential characteristics of the invention. The scope of the invention is intended to encompass all such modifications and variations as come within the scope of the following claims.

I claim:

1. A hemostatic composition comprising: (a) a hemostatic agent selected from the group consisting of ferric sulfate, ferric subsulfate and mixtures thereof; (b) aluminum chloride; (c) aluminum ammonium sulfate; and (d) regenerated oxidized cellulose; wherein components (a), (b), (c) and (d) are present in effective hemostatic amounts.

2. A hemostatic composition as defined in claim 1 wherein said composition further comprises absorbable gelatin.

3. A hemostatic composition as defined in claim 1 wherein said composition also comprises a solvent, said solvent present in sufficient quantity to provide the composition with a paste consistency.

4. A hemostatic composition as defined in claim 2, wherein said composition also comprises a solvent, said solvent present in sufficient quantity to provide the composition with a paste consistency.

5. A hemostatic composition as defined in claim 4, wherein said solvent is saline solution.

6. A hemostatic composition as defined in claim 4 wherein said solvent is a local anesthetic solution.

7. A hemostatic composition comprising, in relative ratios: about 3.3 to about 3.9 grams ammonium aluminum sulfate, about 0.07 to about 0.13 grams oxidized regenerated cellulose, about 0.05 to about 0.07 grams absorbable gelatin, about 6 to about 10 cc of 14.5 to 21.5 wt % ferric sulfate (sub.)solution; and about 6 to about 10 cc of 20 to 30 wt % aluminum chloride solution.

8. A hemostatic composition as defined in claim 7 wherein said composition further comprises about 2 to about 3 cc of 0.9 wt % saline solution.

* * * * *